United States Patent [19]
Negus et al.

[11] Patent Number: 5,897,550
[45] Date of Patent: *Apr. 27, 1999

[54] SENSOR SYSTEM FOR DETECTING CONCEALED BLOOD VESSELS

[75] Inventors: Charles Christopher Negus, Taunton; Robert I. Rudko, Holliston; Stephen J. Linhares, Taunton; Eileen A. Woodruff, Millis, all of Mass.

[73] Assignee: PLC Medical Systems, Inc., Franklin, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/761,987

[22] Filed: Dec. 11, 1996

[51] Int. Cl.$^6$ ..................................................... A61B 17/36
[52] U.S. Cl. .................................. 606/10; 606/13; 606/2
[58] Field of Search .............................. 606/2, 7, 10–15; 607/88, 89, 92; 600/481, 500, 501

[56] References Cited

U.S. PATENT DOCUMENTS

| | | | |
|---|---|---|---|
| 3,782,365 | 1/1974 | Pinna | 600/481 |
| 4,576,177 | 3/1986 | Webster, Jr. | 606/15 |
| 4,976,710 | 12/1990 | Mackin | 607/88 |
| 5,360,426 | 11/1994 | Muller et al. | 606/10 |
| 5,554,152 | 9/1996 | Aita et al. | 606/7 |
| 5,575,787 | 11/1996 | Abela et al. | 606/11 |
| 5,607,421 | 3/1997 | Jeevanandam et al. | 606/7 |
| 5,672,170 | 9/1997 | Cho et al. | 606/13 |
| 5,700,259 | 12/1997 | Negus et al. | 606/13 |

OTHER PUBLICATIONS

Tekscan Inc., "Tekscan Pressure Measurement Systems Brochure," South Boston, MA, Jun. 1995.
Iversen, "Tactile Sensing, 1990s Style," Assembly Magazine, pp. 23–26, Feb. 1993.

*Primary Examiner*—Michael Peffley
*Assistant Examiner*—Bryan K. Yarnell
*Attorney, Agent, or Firm*—Iandiorio & Teska

[57] ABSTRACT

A sensor system for detecting concealed blood vessels including a handpiece having a passage for transmitting a laser beam and a detector housing at the distal end of the handpiece, the housing including a common electrode, a plurality of segmented electrodes spaced from the common electrode and between the common electrode and the segmented electrodes a plurality of four sensitive elements having an electrical characteristic which varies with the force applied; and an indicator device responsive to variations in the electrical characteristic for representing the presence of a concealed vessel.

18 Claims, 12 Drawing Sheets

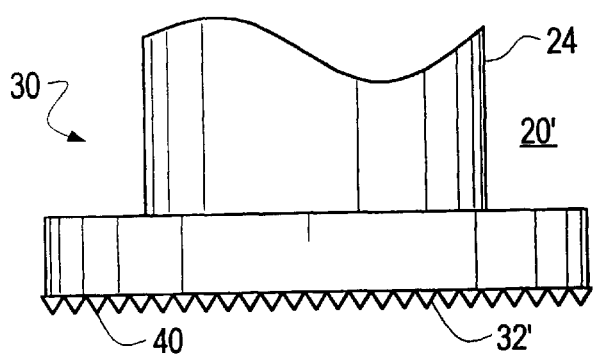
FIG. 5A
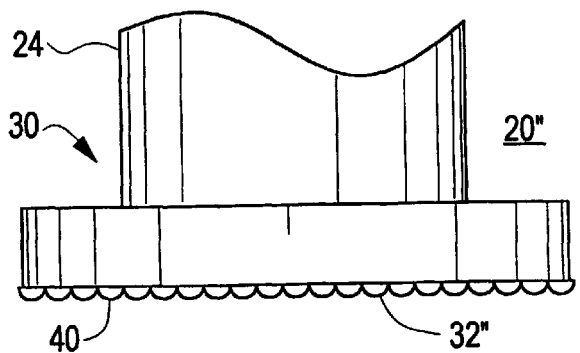
FIG. 5B
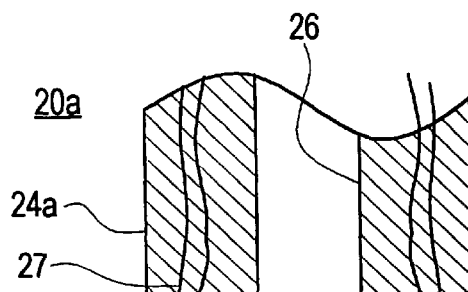
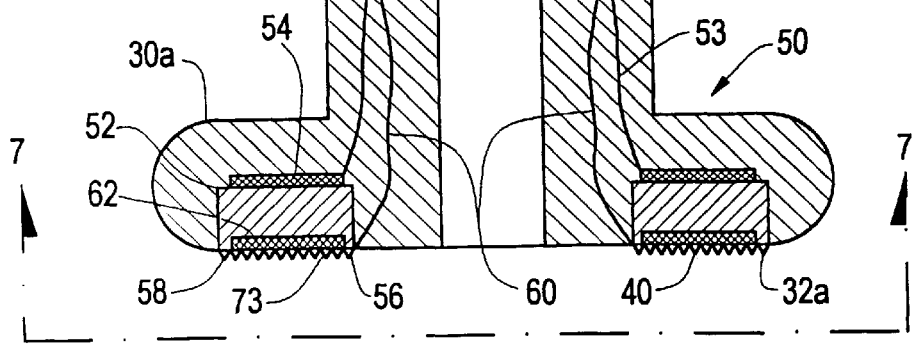
FIG. 6

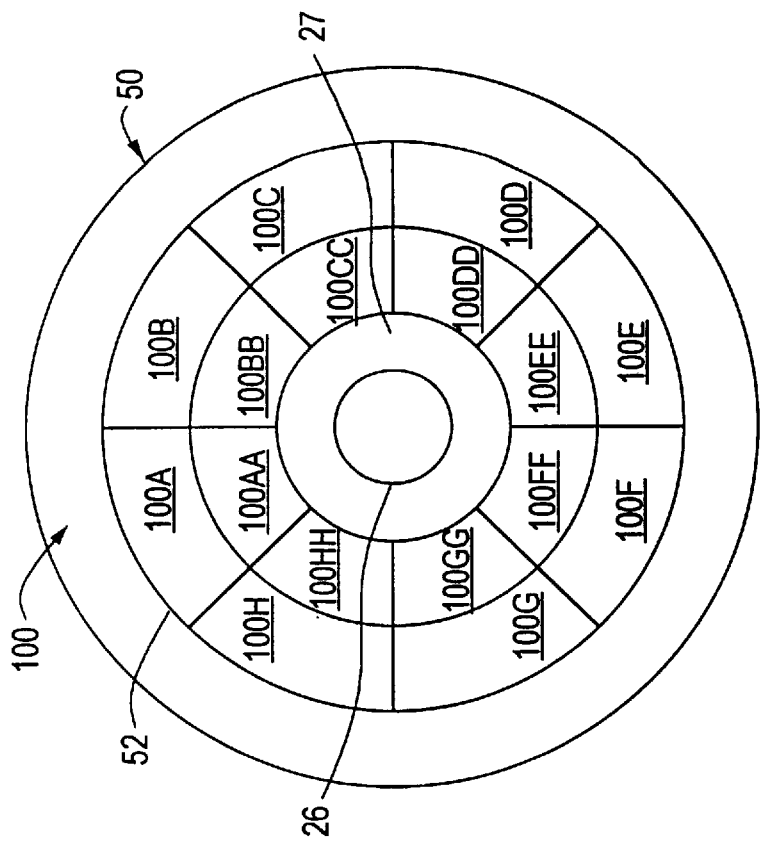
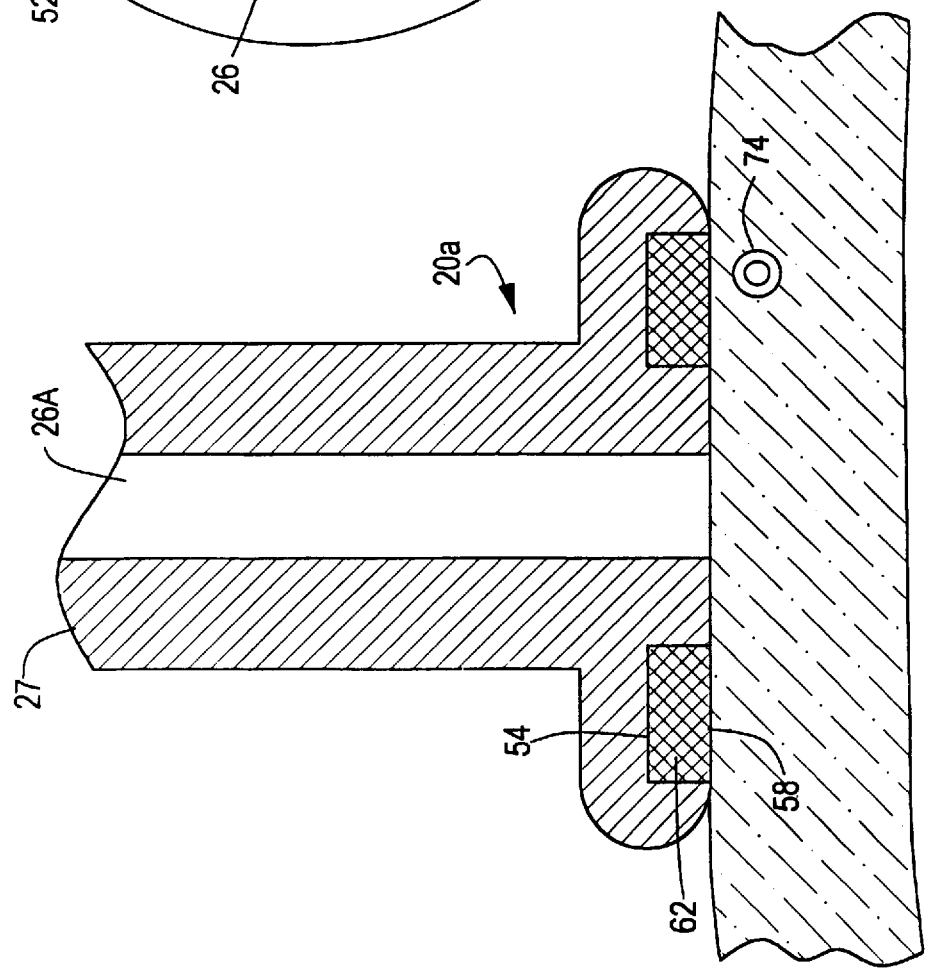
FIG. 11
FIG. 10

SENSOR SYSTEM FOR DETECTING CONCEALED BLOOD VESSELS

FIELD OF INVENTION

This invention relates to a sensor system for detecting concealed coronary blood vessels, and more particularly to such a system for detecting concealed coronary blood vessels, especially in transmyocardial revascularization.

BACKGROUND OF INVENTION

The unexpected encountering of a concealed blood vessel in surgery can have disastrous results. For example, in conventional open heart transmyocardial revascularization (TMR) a channel is created through the heart wall from the outside to the inside of the left ventricle using a laser beam typically from a $CO_2$ laser. The channel heals quickly on the outside from slight finger pressure so there is no substantial bleeding. The channel remains open on the inside part way through the heart wall so that the heart muscle is supplied with blood by suffusion through the channel from within the ventricle. With a number of such channels the blood supply to the heart muscle can be restored to ensure proper functioning of the heart despite occluded coronary arteries. One problem encountered in TMR is the danger of creating a channel in a path which cuts an unseen vessel in the heart wall. When this occurs substantial bleeding can occur so that a stitch will be required on the outside of the channel at the heart wall to stanch the bleeding. In addition to the obvious danger and extra effort required, this technique also results in a less extensive channel. That is, channels which have such a stitch tend to heal for a longer distance into the heart wall thereby shortening the channel where the blood flows and reducing that area of the heart muscle suffused.

SUMMARY OF INVENTION

It is therefore an object of this invention to provide a sensor system for detecting concealed blood vessels.

It is a further object of this invention to provide a sensor system for detecting concealed coronary blood vessels in transmyocardial revascularization.

It is a further object of this invention to provide such a system which is simple, reliable and integratable with present transmyocardial revascularization laser devices.

The invention results from the realization that a reliable, effective sensor system for detecting concealed blood vessels can be achieved using a plurality of force sensitive elements to sense the force of blood pulsing in a blood vessel to indicate the presence of even an unseen vessel.

This invention features a sensor system for detecting concealed coronary blood vessels in transmyocardial revascularization. There is a handpiece including a passage for transmitting a laser beam that effects the transmyocardial revascularization. There is also a detector housing at the distal end of the handpiece. The housing includes a common electrode, a plurality of segmented electrodes spaced from the common electrode, and between the common electrode and the segmented electrodes a plurality of force sensitive elements having an electrical characteristic which varies with the force applied. An indicator device responsive to variations in the electrical characteristic represents the presence of a coronary vessel concealed in the heart wall.

In a preferred embodiment the force sensitive elements may include a piezoelectric medium and the electrical characteristic may be voltage output. The force-sensitive elements may include a resistive medium and the electrical characteristic may be resistance. The force-sensitive elements may include a capacitive medium and the electrical characteristic may be capacitance. One of the electrodes may be at the distal end of the housing and the distal end of that electrode may be coated with a nonconductive material for contacting the heart. The indicator device may include a signal processing circuit responsive to varying electrical characteristics for generating signals representative of the force sensed by each element and an indicator device responsive to the signals for representing the presence of a concealed coronary vessel. The indicator device may include a visual display.

This invention also features a sensor system for detecting any concealed blood vessels. There is a handpiece including a passage for transmitting a laser beam and a detector housing at the distal end of the handpiece. The housing includes a common electrode, a plurality of segmented electrodes spaced from the common electrode, and between the common electrode and the segmented electrodes a plurality of force sensitive elements having an electrical characteristic which varies with the force applied. An indicator device responsive to variations in the electrical characteristic represents the presence of a concealed vessel.

In a preferred embodiment the force sensitive elements may include a piezoelectric medium and the electrical characteristic may be voltage output. The force-sensitive elements may include a resistive medium and the electrical characteristic may be resistance. The force-sensitive elements may include a capacitive medium and the electrical characteristic may be capacitance. One of the electrodes may be at the distal end of the housing and the distal end of that electrode may be coated with a nonconductive material. The indicator device may include a signal processing circuit responsive to varying electrical characteristics for generating signals representative of the force sensed by each element and an indicator device responsive to the signals for representing the presence of a concealed vessel. The indicator device may include a visual display.

DISCLOSURE OF PREFERRED EMBODIMENT

Other objects, features and advantages will occur to those skilled in the art from the following description of a preferred embodiment and the accompanying drawings, in which:

FIG. 5A is a side elevational view of a portion of the handpiece showing a roughened surface with pyramidical bumps;

FIG. 5B is a view similar to FIG. 5A with lenticular bumps making up the roughened surface;

FIG. 6 is a side elevational sectional view of a handpiece employing a portion of the sensor system for detecting concealed coronary blood vessels in transmyocardial revascularization according to this invention;

FIG. 10 is a side sectional view of the handpiece of FIG. 9 showing a concealed blood vessel in the heart wall which the system is capable of detecting;

FIG. 11 is a bottom plan view of a sensor system according to this invention similar to that shown in FIG. 7 with an alternative segmentation of the force sensitive elements;

This embodiment shows the concealed blood vessel sensor system of this invention, particularly applied for detecting concealed coronary blood vessels during transmyocardial revascularization.

Figure 1:
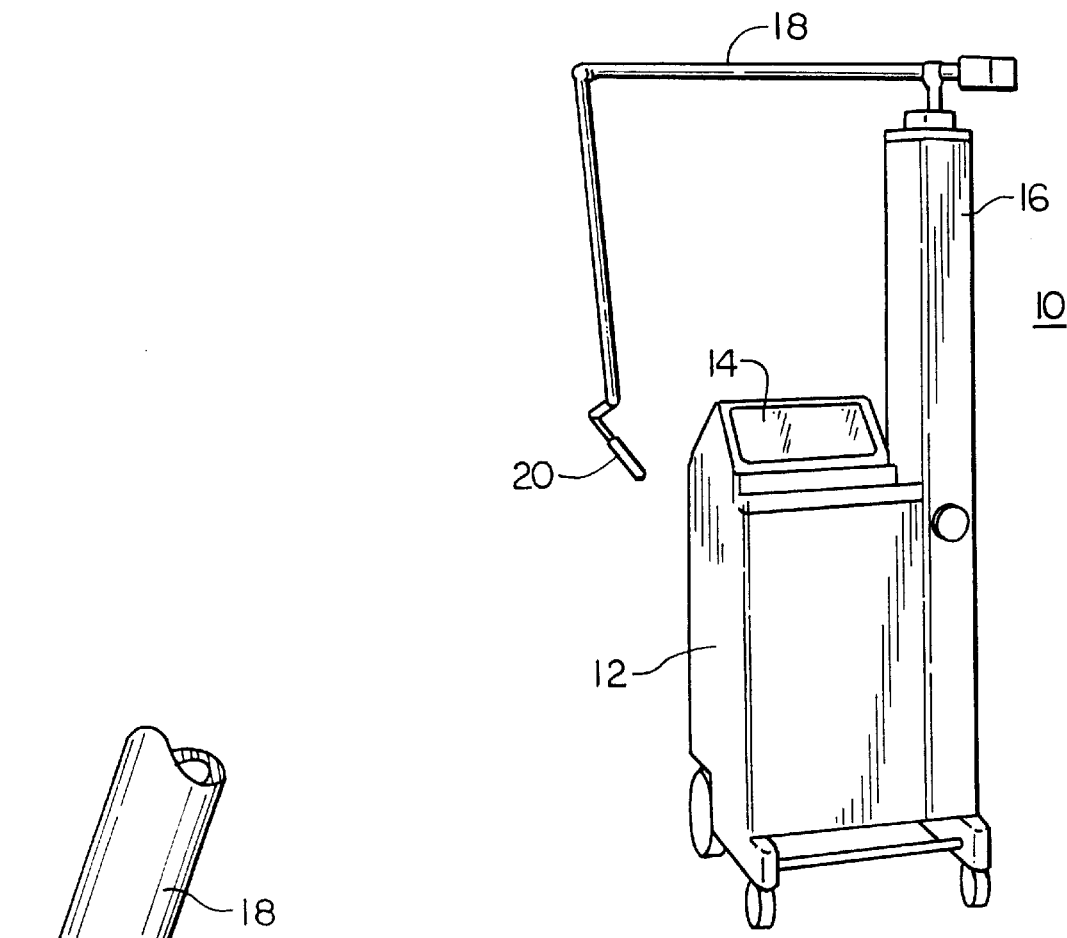
FIG. 1 is a three-dimensional view of a $CO_2$ laser system employing a handpiece according to this invention.
Figure 2:
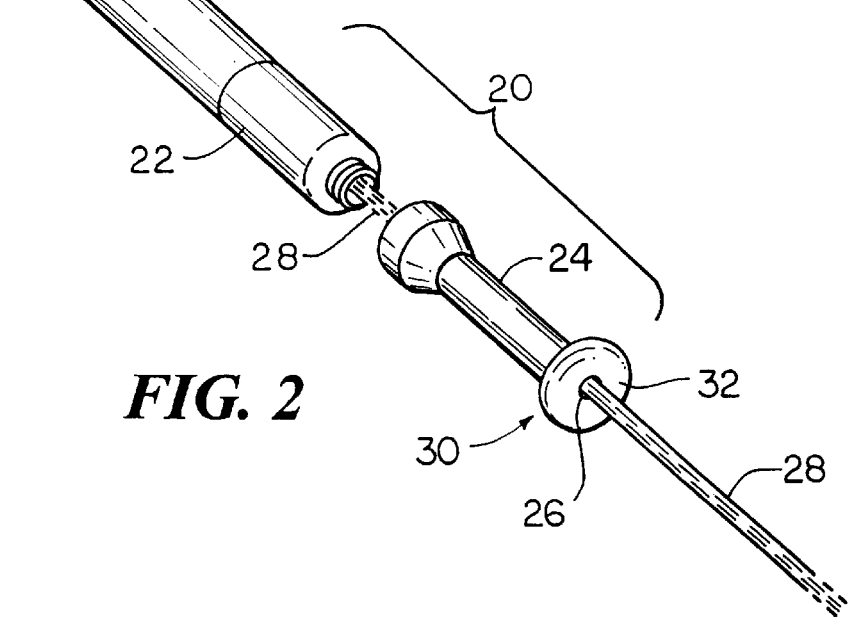
FIG. 2 is an enlarged view of a handpiece according to this invention and a portion of the articulated optical arm which carries it.

There is shown in FIG. 1 a surgical laser system 10 including a power supply 12 and control panel 14 for operating $CO_2$ laser 16, whose output beam is directed through a lens unit 22, FIG. 2, including a lens for focusing the laser beam and a barrel 24 which includes an aperture 26 through which the laser beam 28 exits. The distal end 30 of barrel 24 includes an enlarged contact surface 32 for contacting the wall of the heart to be perforated by the laser beam. Surface 32 is relatively large to minimize the contact pressure between it and the heart wall, and is generally flat with a non-skid texture with rounded edges. Surface 32 is typically 1 cm or greater in diameter, and may be electrically and thermally insulating.

Figure 3:
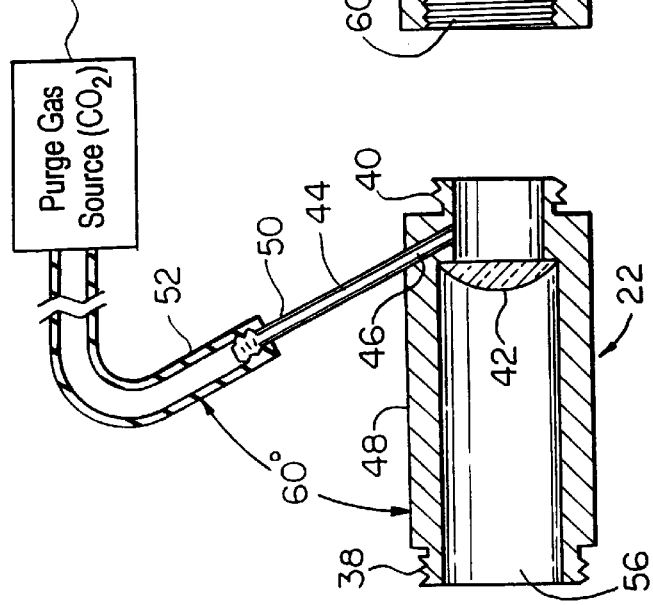
FIG. 3 is an enlarged cross-sectional view of the focusing lens section of the handpiece of FIGS. 1 and 2.

The focusing unit or lens unit 22, FIG. 3, includes a threaded portion 38 for interconnection with arm 18, and a threaded portion 40 which interconnects with barrel 24. Carried within unit 22 is focusing lens 42. An inlet tube 44 is joined by interference fit with bore 46 and a cylindrical wall 48 of unit 22. At its free end 50, inlet 44 is connected to a hose 52 which is in turn connected to a purge gas source 54 which provides a gas such as $CO_2$ under gentle pressure to create a backflow from lens 42 forward into barrel 24. This keeps any debris from the vaporization from contacting and obscuring or damaging lens 42. Lens 42 is positioned directly in line with passage 56 provided in unit 22 for propagation of the laser beam. Threads 40 of lens unit 22 engage with threads 60 of barrel 24, FIG. 4, which also includes a passage 62 communicates with laser aperture 26 to create a clear passage for the propagation of laser beam 28 to wall 66 of a beating heart. Lens 42 focuses the laser beam proximate aperture 26 and surface 32.

Figure 4:
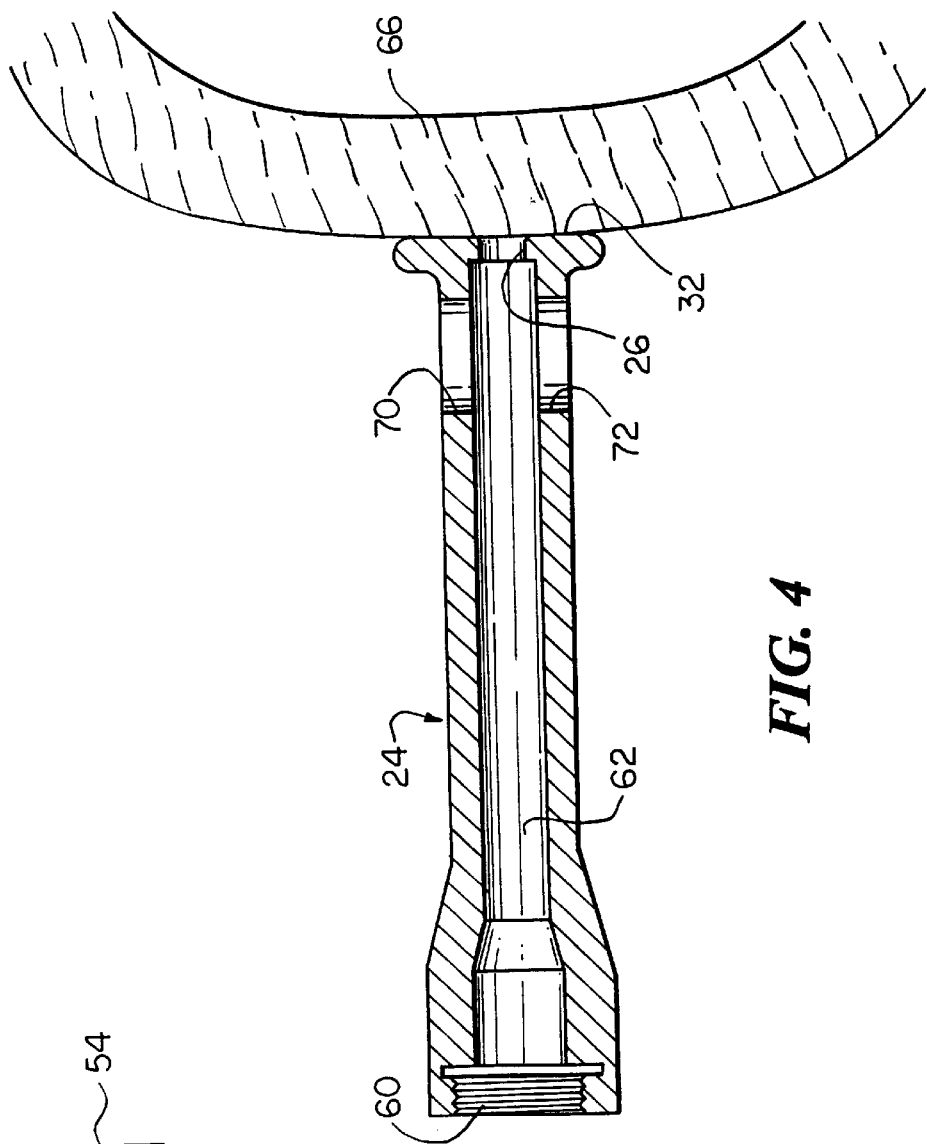
FIG. 4 is an enlarged sectional view of the barrel of the handpiece of FIGS. 1 and 2.

As can be seen clearly in FIG. 4, contact surface 32 is considerably broader than the cross-sectional area of barrel 24 alone and is formed in the shape of a flange with surface 32 being smooth and flat and all the edges rounded. This increases the area of contact with the heart, and therefore decreases the pressure or force per unit area on the heart. It also provides a more stable platform by which to maintain perpendicularity between the beam 28 and the heart wall 66. Thus this construction provides the necessary precision in locating the focus of the beam on the heart wall without interfering with the heart operation or its electrical activity. Barrel 24 includes vent holes 70, 72 for exhausting the purging gas and trapped debris away from the lens 42 and away from aperture 26.

Although thus far the surface 32 at the distal end 30 of handpiece 20 is shown as smooth, it is often desirable to have a roughened or gripping surface to prevent movement of the handpiece once it is in position and ready for firing of the laser. For example, in FIG. 5A surface 32' is formed of pyramidical bumps 40. In FIG. 5B surface 32" includes bumps 42 that are lenticular.

In accordance with this invention, handpiece 20a, FIG. 6, includes at its distal end 30a a housing 50 having a recess 52 in which is located a common electrode 54 and a plurality of segmented electrodes 56. An insulation coating 58 is applied to segmented electrodes 56 to prevent the electrical portion of the circuit from coming in contact with the heart. A wire 60 from each of the segmented electrodes and one wire 53 from the common electrode 54 are disposed in barrel 24a and led back to the remainder of the circuitry in the sensor system. Between the segmented electrodes 56 and the common electrode 54 is a medium 62 that has an electrical characteristic that changes with the force applied to it. For example, a piezoelectric material may be used in which the voltage output generated by the piezoelectric is a function of the force applied to the piezoelectric crystal or medium 62 may be a material that changes resistance or any other impedance quality with applied force, e.g., it may be a capacitive material which changes capacitance with the applied force. Electrical insulation 73 such as polyurethane is located on surface 32 to insulate the lower electrode, be it segmented or common, from the electric fields of the heart.

Figure 7:
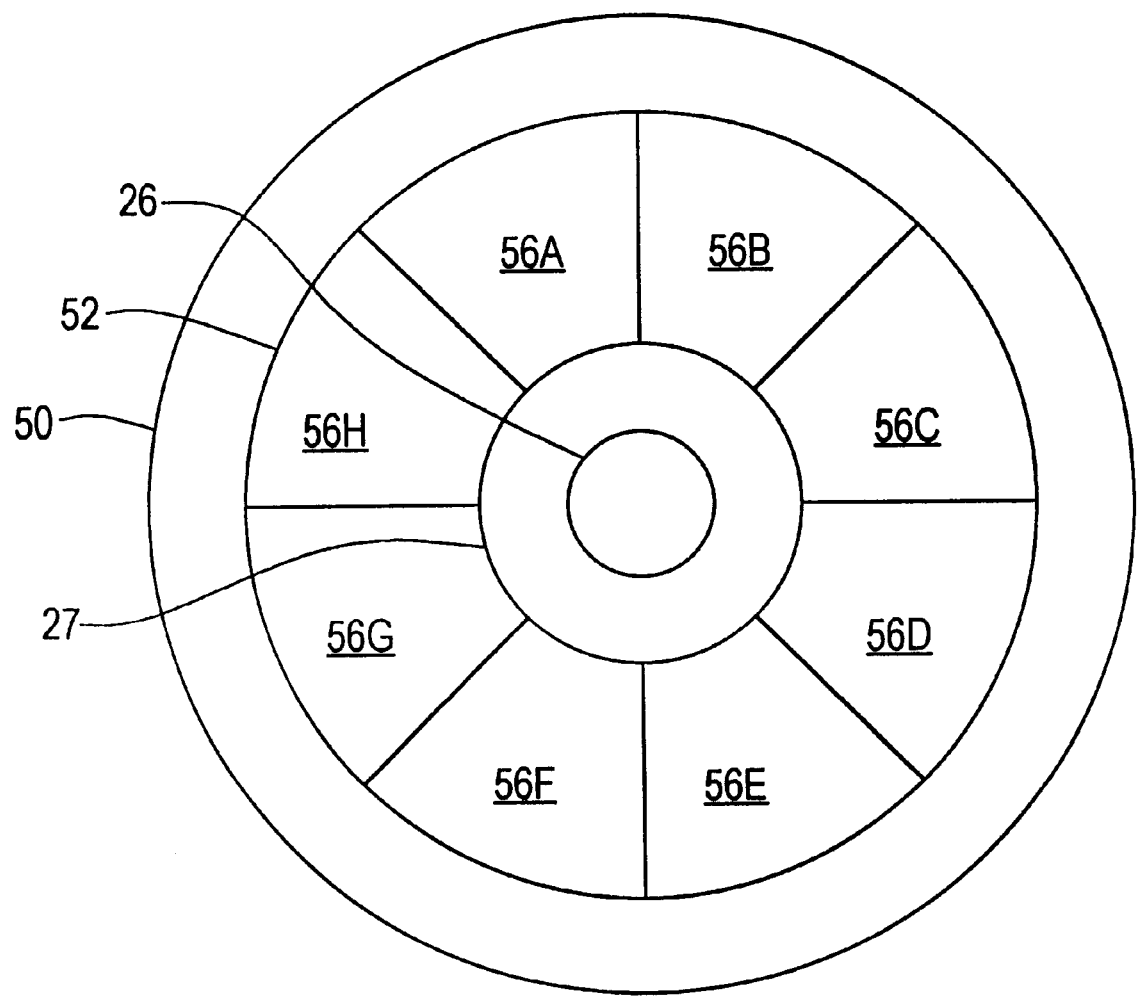
FIG. 7 is a sectional view taken along line 7—7 of FIG. 6 showing force sensitive elements having pie shaped sectors.
Figure 8:
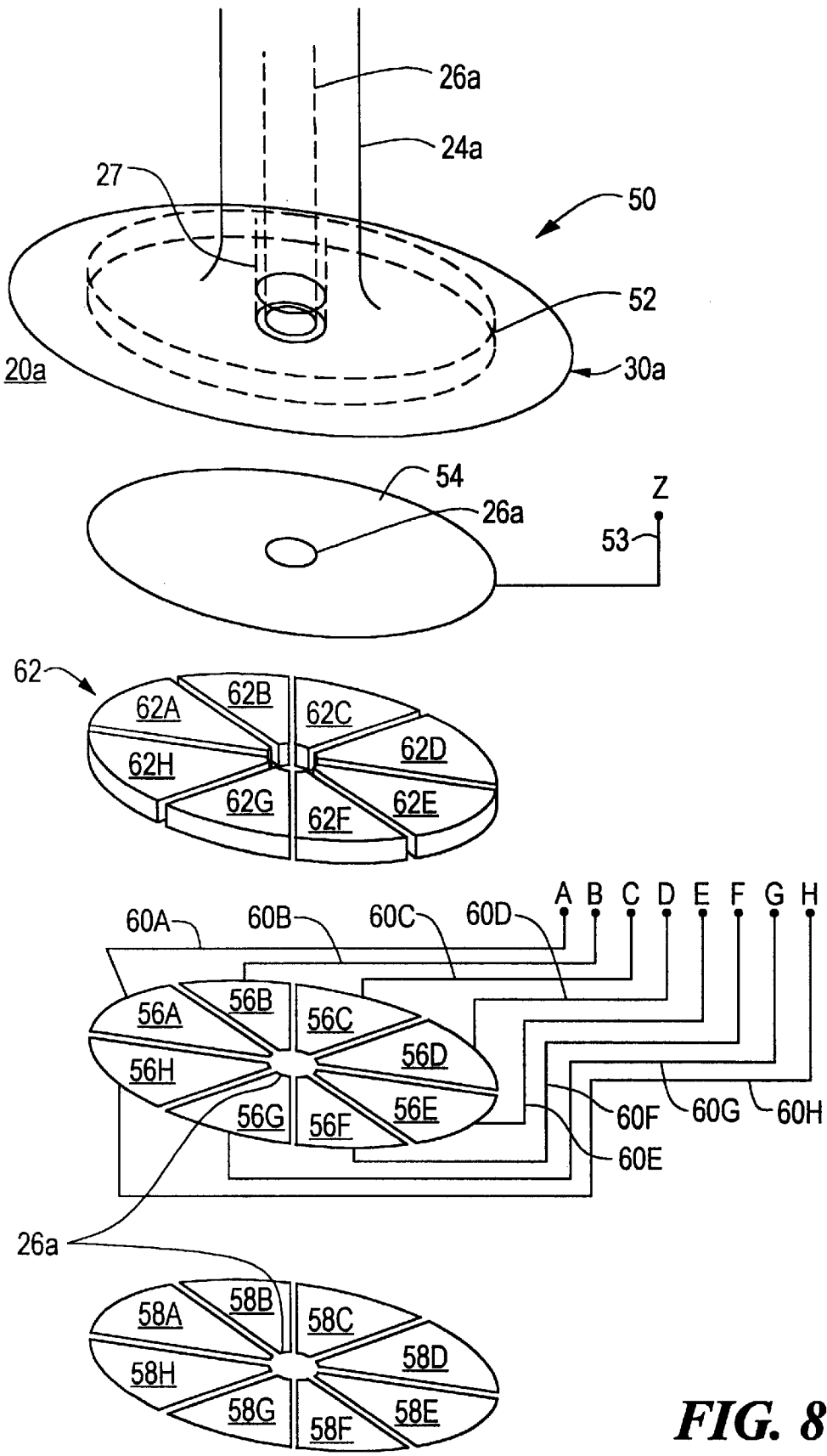
FIG. 8 is an exploded three-dimensional view of a sensor system according to this invention.

The structure of segmented electrodes 56 can be seen more readily in FIG. 7 where the eight segments 56A–H are plainly visible. A fuller understanding of the construction can be had from FIG. 8, where in that exploded view common electrode 54 is connected over line 53 to connection point Z while segmented electrodes 56A–H are connected over lines 60 to points A–H.

Although in the figures the common electrode 54 has been shown on top and the segmented electrodes 56 have been shown at the distal end of handpiece 20a, this is not a necessary limitation of the invention as the segmented and common electrodes may well be interchanged. In fact, in some applications it may be advantageous to place the segmented electrodes 56 which involve a harness of wires on top and locate common electrode 54 at the distal end.

Figure 9:
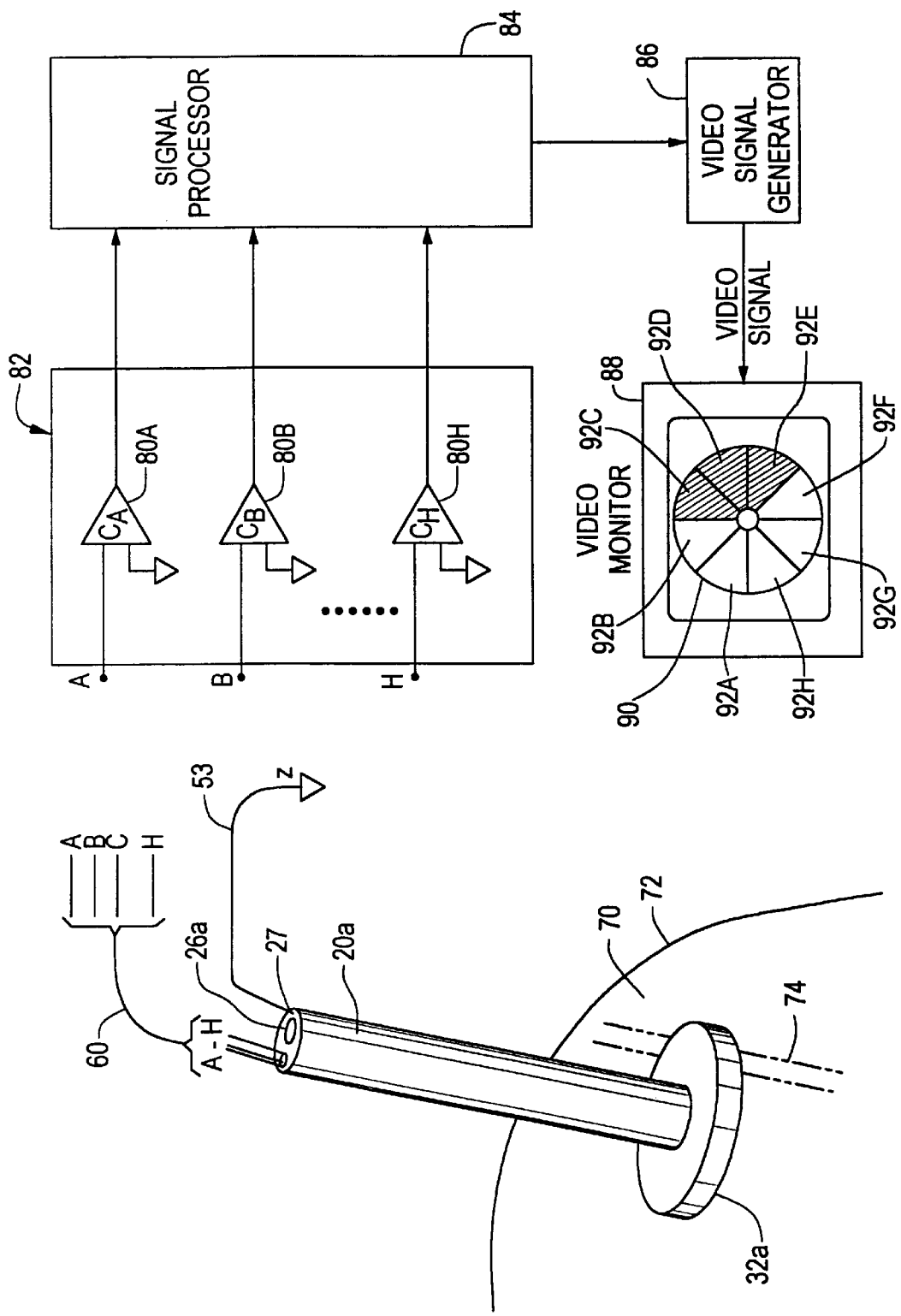
FIG. 9 is a schematic block diagram showing a sensor system according to this invention including a handpiece disposed on a heart wall for sensing concealed blood vessels and effecting transmyocardial revascularization and the electronic processing circuitry for providing a video display.

In operation, handpiece 20a is placed with its surface 32a against the wall 70, FIG. 9, of heart 72 so that it partially covers concealed coronary blood vessel 74. The concealed position of vessel 74 can be seen from a different vantage point in FIG. 10. The outputs from line 60 are delivered to the A–H inputs through the comparator circuits 80A–H in comparator circuit 82. With the conductor 53 from common electrode 54 connected to ground (or a reference potential) and the comparators 80A–H connected to ground (or a similar reference potential), each of the comparators 80A–H may provide a monolevel or multilevel thresholded output. For example, each comparator may have three outputs representing light gray, dark gray and black video displays, depending upon the force being sensed by the respective force sensing element 62A–H. The output signals from comparators 80A–H are processed in signal processor 84 and converted to a video signal by video signal generator 86 which is used to drive video monitor 88 to produce a replica 90 of the segmented structure of the force sensing elements 62. Thus with the concealed blood vessel 74 in the position shown in FIGS. 9 and 10 the force or pressure exerted by the blood pulsing in vessel 74 produces an increased signal that causes segments 92C, D and E of image 90 to be for example a dark gray while the remainder of the segments 92A and B and 92F, G and H remain light gray. This tells the operating surgeon that there is a concealed coronary vessel in the area beneath that portion of handpiece 20*a*.

Although thus far the segmented electrodes 56 and force sensing medium 62 have been shown as simple pie-shaped sectors, this is not a necessary limitation of the invention. For example, as shown in FIG. 11 the segmentation for example may separate the medium 62 and the segmented electrodes 56 both radially and circumferentially as shown in FIG. 11, where each of the segmented electrodes 100 is divided into two sections 100A, 100AA, 100B, 100BB, 100C, 100CC, 100D, 100DD, 100E, 100EE, 100F, 100FF, 100G, 100GG, 100H, 100HH about cable channel 27.

Figure 12:
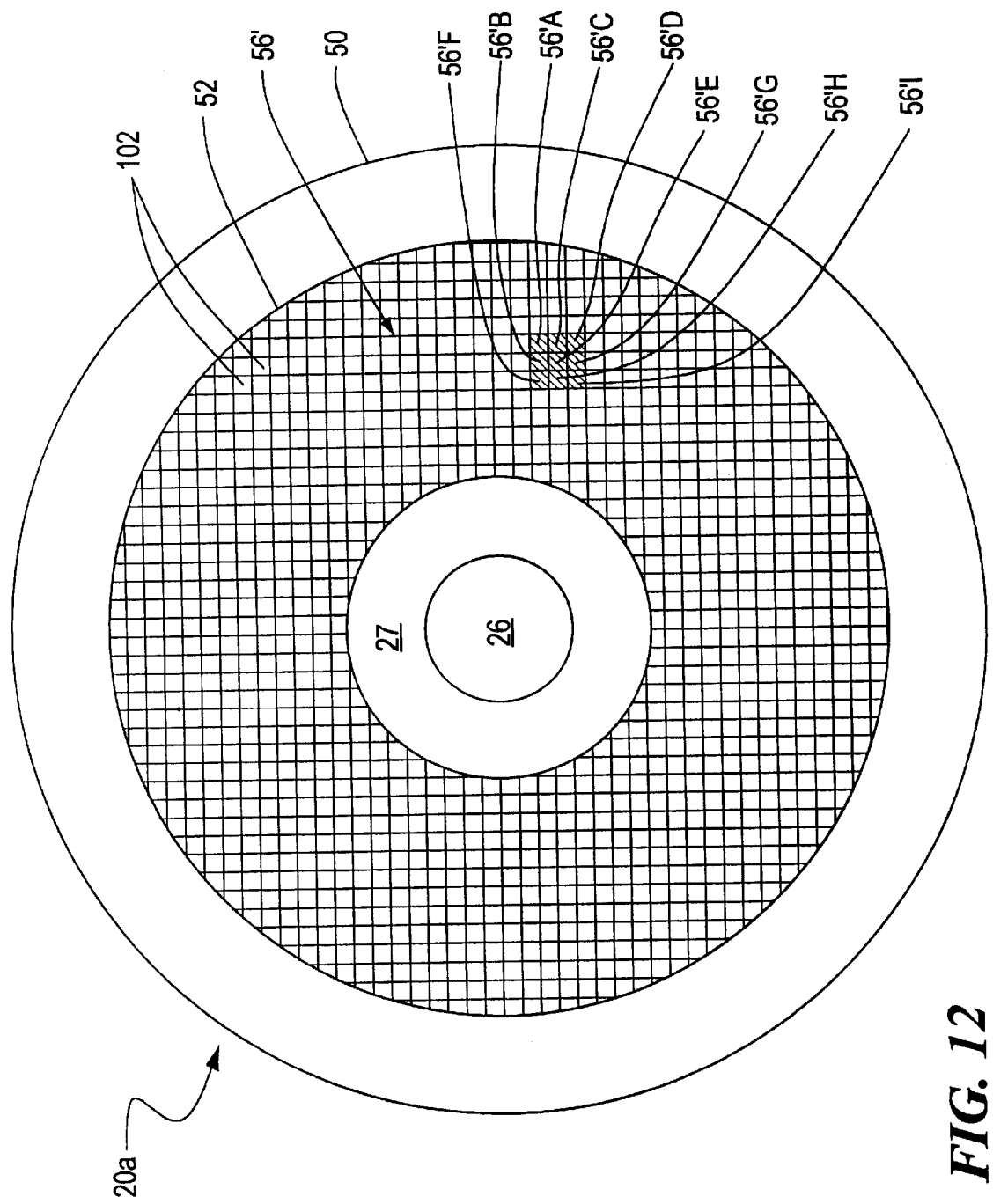
FIG. 12 is a bottom plan view similar to FIGS. 7 and 11 using a different construction for the force-sensitive mediums.

In yet another construction, a finer resolution may be obtained by dividing the segmented electrodes 56', FIG. 12, into a matrix of rows and columns of individual pixels 102.

Figure 13:
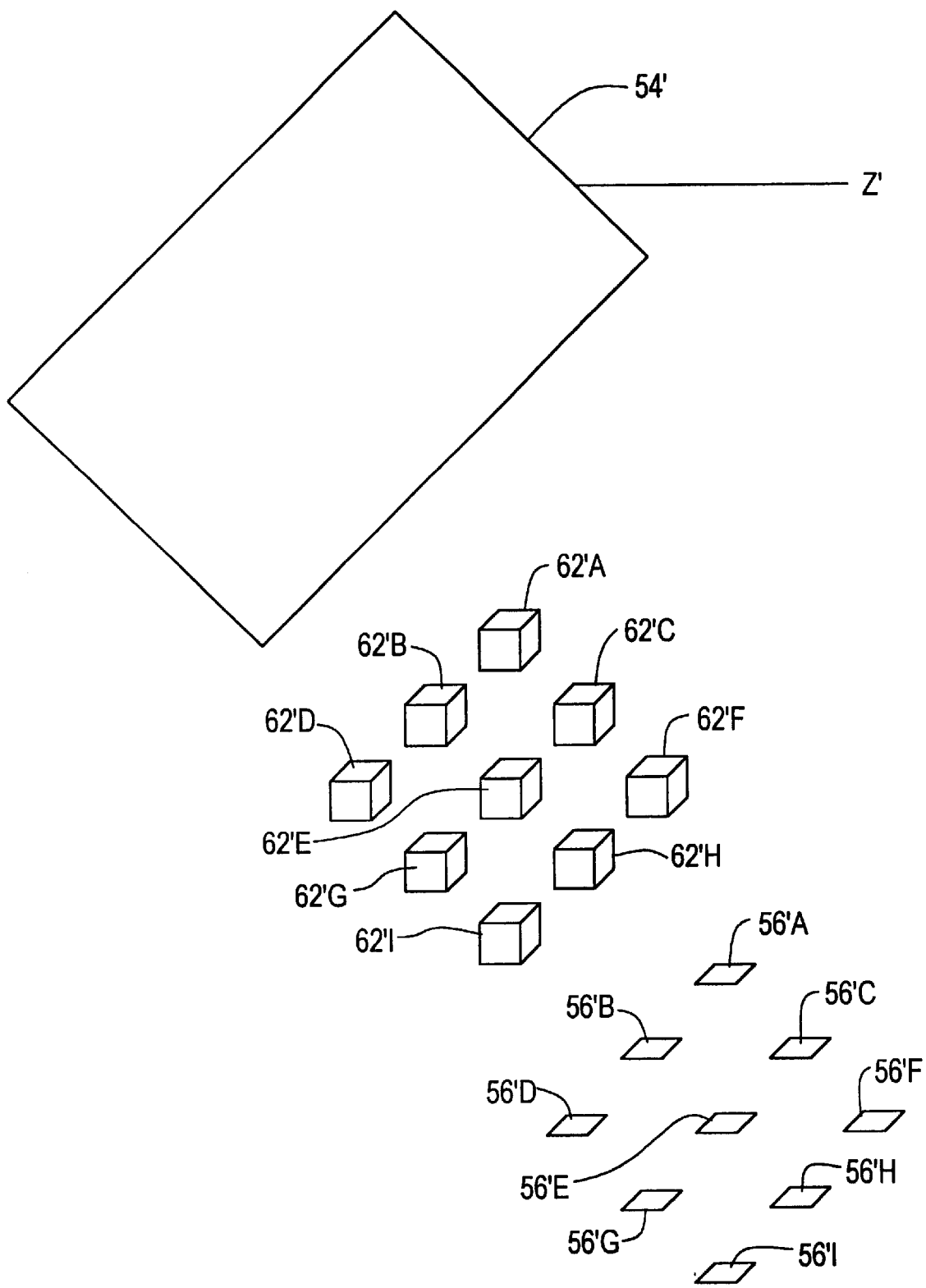
FIG. 13 is an exploded three-dimensional view of a portion of the sensor system showing the wiring of the segmented electrodes.

The structure associated with nine of the segmented electrodes 56'A–I shown in FIG. 12 has been exploded in FIG. 13 to show the relationship of the common electrode 54' to force sensing mediums 62'A–I, and the segmented electrodes 56'A–I.

Figure 14:
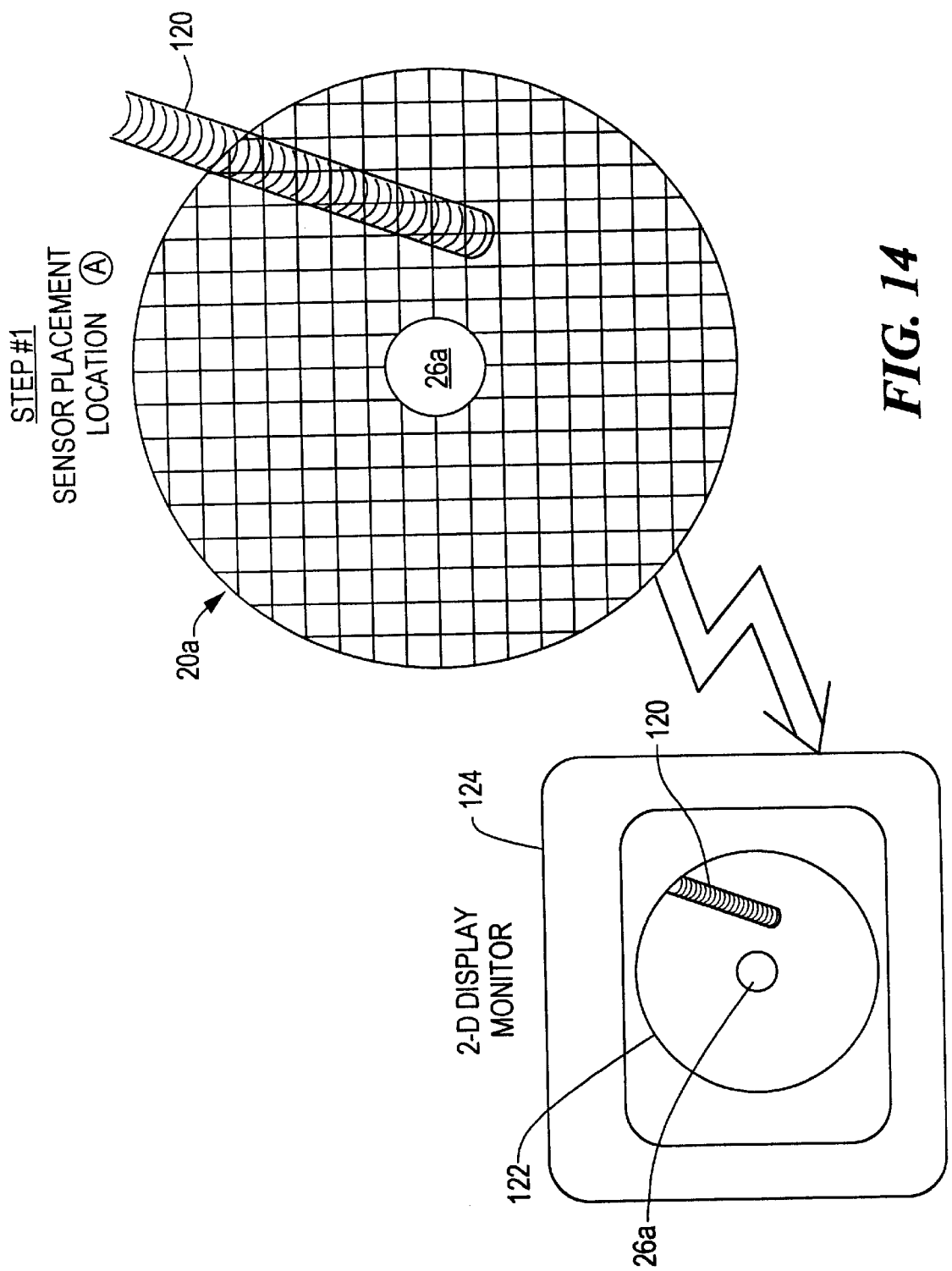
FIG. 14 is a diagrammatic view of the placement of the handpiece and sensor system according to this invention over a concealed blood vessel and its display on a display monitor.
Figure 15:
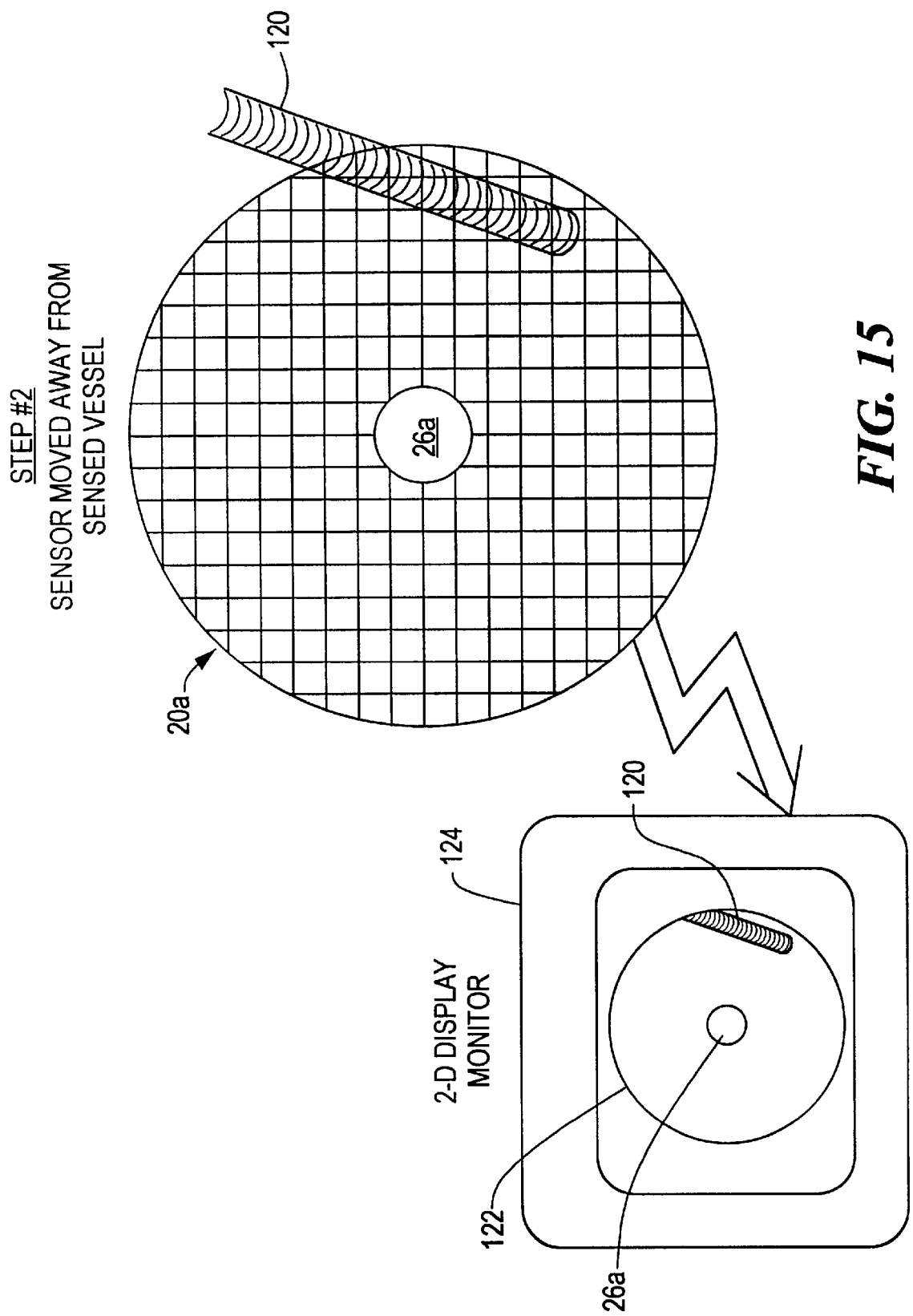
FIG. 15 is a view similar to FIG. 14 with the handpiece and sensor system moved slightly to avoid the concealed blood vessel.

The manner in which such a device would be used is depicted in FIGS. 14 and 15 where concealed blood vessel 120, FIG. 14, is quite close to the center aperture 26*a* through which the laser beam 28 passes as depicted on screen 122 of display monitor 124. Seeing this the surgeon would move handpiece 20*a* to the left as shown in FIG. 15, so that the center aperture 26*a* is moved farther away from concealed coronary vessel 120 which again is depicted on screen 122 of monitor 124 in FIG. 15, thus clearing the way for the surgeon to fire the laser and create a channel free from fear that it may puncture or cut coronary vessel 120.

Figure 17:
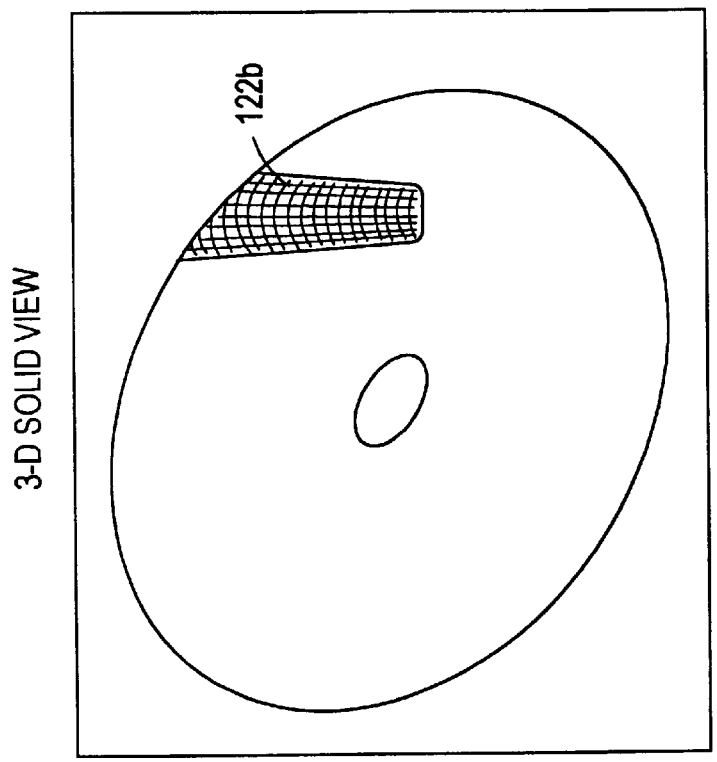
FIG. 17 is a view similar to FIG. 16 using a three-dimensional solid view technique.
Figure 16:
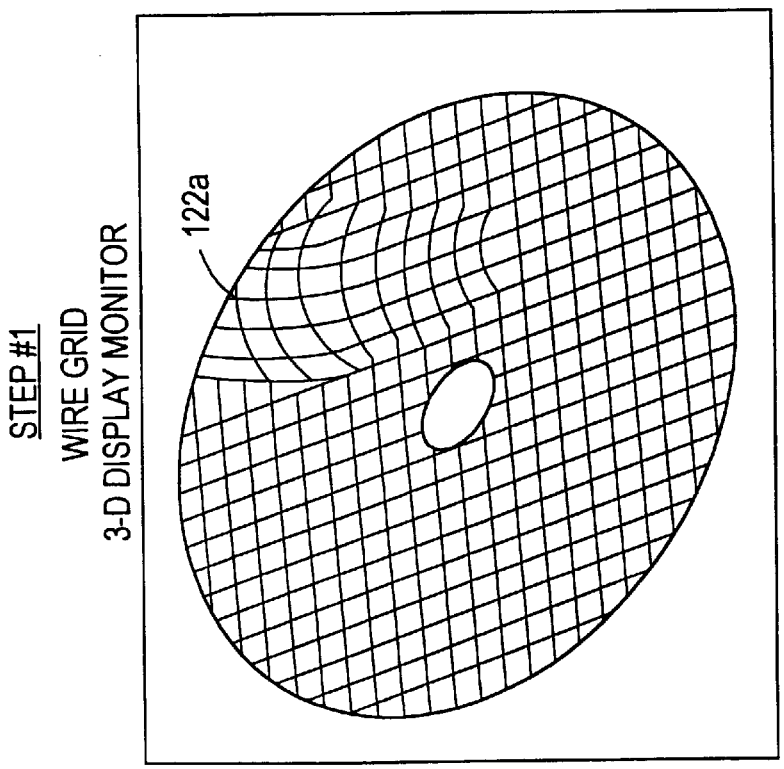
FIG. 16 illustrates a high-resolution three-dimensional video display of the concealed blood vessel of FIGS. 14 and 15 using a wire grid three-dimensional display technique.

Although thus far the depiction of the concealed artery has been done in two dimensions, more sophisticated imaging techniques can be applied to the output data from the signal processor to create a three-dimensional view of coronary 122*a*, FIG. 16, using wire grid three-dimensional display techniques or a three-dimensional solid view technique may be used to obtain the illustration 122*b*, FIG. 17, of the concealed coronary vessel.

Although thus far the display has been illustrated in the enclosed embodiments as being a visual and even more specifically a graphic or pictorial representation, this is not a necessary limitation of the invention as other sorts of indicators such as lights which change their intensity or color or sounds which change their pitch or volume, may be used to alert the surgeon that he must move the handpiece before firing the ablative laser in order to avoid the possibility of cutting or puncturing a coronary blood vessel.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A sensor system for detecting concealed coronary blood vessels in a heart wall during transmyocardial revascularization, the system comprising:

a handpiece including a passage for transmitting a laser beam;

detector means located at a distal end of said handpiece for sensing the presence of a coronary vessel in the heart wall, said detector means including:

a reference electrode, and force sensing means for producing an increased signal in response to blood pulsing in a concealed coronary blood vessel; and an indicator device responsive to said increased signal for representing the presence of a coronary vessel in the heart wall.

2. The system of claim 1 in which the force sensing means includes a plurality of segmented electrodes spaced from the reference electrode and a plurality of force sensitive elements having an electrical characteristic which varies with an applied force, said force sensitive elements disposed between said reference electrode and the plurality of segmented electrodes.

3. A sensor system for detecting concealed coronary blood vessels in transmyocardial revascularization comprising:

a handpiece including a passage for transmitting a laser beam; and a detector housing at the distal end of said handpiece; said housing including a detector having a characteristic which varies with the applied; and an indicator device responsive to variations in said characteristic for representing presence of a coronary vessel concealed in the heart wall.

4. The sensor system of claim 3 in which said detector includes a common electrode, a plurality of segmented electrodes spaced from said common electrode and between said common electrode and said segmented electrodes a plurality of force sensitive elements and said characteristic is an electrical characteristic.

5. The sensor system of claim 4 in which said force sensitive elements include a piezoelectric medium and said electrical characteristic is voltage output.

6. The sensor system of claim 4 in which said force sensitive elements include a resistive medium and said electrical characteristic is resistance.

7. The sensor system of claim 4 in which said force sensitive elements include a capacitive medium and said electrical characteristic is capacitance.

8. The sensor system of claim 4 in which one of said electrodes is at the distal end of said housing and the distal end of said one electrode is coated with a nonconductive material.

9. The sensor system of claim 3 in which said indicator device includes a signal processing circuit responsive to said varying characteristic for generating signals representative of the force sensed by said sensor and a display device responsive to said signals for representing the presence of a concealed coronary vessel.

10. The sensor system of claim 9 in which said display device includes a visual display.

11. A sensor system for detecting concealed blood vessels comprising:

a handpiece including a passage for transmitting a laser beam; and a detector housing at a distal end of said handpiece; said housing including a sensor having a characteristic which varies with the forced applied; and an indicator device responsive variations in said characteristic for representing the presence of a concealed vessel.

12. The sensor system of claim 11 in which said sensor includes a common electrode, a plurality of segmented electrodes spaced from said common electrode and between said common electrode and said segmented electrodes a plurality of force sensitive elements and said characteristic is an electrical characteristic.

13. The sensor system of claim 12 in which said force sensitive elements include a piezoelectric medium and said electrical characteristic is voltage output.

14. The sensor system of claim 12 in which said force sensitive elements include a resistive medium and said electrical characteristic is resistance.

15. The sensor system of claim 12 in which said force sensitive elements include a capacitive medium and said electrical characteristic is capacitance.

16. The sensor system of claim 12 in which one of said electrodes is at the distal end of said housing and the distal end of said one electrode is coated with a nonconductive material.

17. The sensor system of claim 11 in which said indicator device includes a signal processing circuit responsive to said varying characteristic for generating signals representative of the force sensed by said sensor and a display device responsive to said signals for representing the presence of a concealed vessel.

18. The sensor system of claim 17 in which said display device includes a visual display.

* * * * *